(12) United States Patent
Dees et al.

(10) Patent No.: US 6,986,740 B2
(45) Date of Patent: Jan. 17, 2006

(54) ULTRASOUND CONTRAST USING HALOGENATED XANTHENES

(75) Inventors: H. Craig Dees, Knoxville, TN (US); Timothy C. Scott, Knoxville, TN (US); Eric A. Wachter, Oak Ridge, TN (US)

(73) Assignee: Xantech Pharmaceuticals, Inc., Knoxville, TN (US)

( * ) Notice: Subject to any disclaimer, the term of this patent is extended or adjusted under 35 U.S.C. 154(b) by 274 days.

(21) Appl. No.: 10/314,840

(22) Filed: Dec. 9, 2002

(65) Prior Publication Data

US 2003/0167006 A1 Sep. 4, 2003

Related U.S. Application Data

(63) Continuation-in-part of application No. 09/184,388, filed on Nov. 2, 1998, now Pat. No. 6,493,570.

(51) Int. Cl.
*A61B 8/00* (2006.01)

(52) U.S. Cl. ........................................ 600/458; 424/9.5
(58) Field of Classification Search ................ 600/458; 424/9.5, 9.51, 9.52
See application file for complete search history.

(56) References Cited

U.S. PATENT DOCUMENTS

| | | | |
|---|---|---|---|
| 3,868,950 A | 3/1975 | Kato | 128/66 |
| 3,986,513 A | 10/1976 | Stuhl | 128/373 |
| 4,172,979 A | 10/1979 | Morrison | 250/505 |
| 4,444,189 A | 4/1984 | Seiverd | 128/395 |
| 4,599,227 A | 7/1986 | Dees et al. | 424/38 |
| 4,691,332 A | 9/1987 | Burstein et al. | 378/7 |
| 4,856,528 A | 8/1989 | Yang et al. | 128/653 |
| 4,973,848 A | 11/1990 | Kolobanov et al. | 250/458.1 |
| 5,008,907 A | 4/1991 | Norman et al. | 378/65 |
| 5,053,006 A | 10/1991 | Watson | 604/52 |
| 5,128,139 A | 7/1992 | Brown et al. | 424/450 |
| 5,149,801 A | 9/1992 | Kahl et al. | 540/145 |
| 5,258,453 A | 11/1993 | Kopecek et al. | 525/54.1 |
| 5,284,831 A | 2/1994 | Kahl et al. | 514/21 |
| 5,368,031 A | 11/1994 | Cline et al. | 128/653 |
| 5,445,608 A | 8/1995 | Chen et al. | 604/20 |
| 5,456,901 A | * 10/1995 | Unger | 424/9.51 |
| 5,462,053 A | 10/1995 | Briggs et al. | 128/653.4 |
| 5,576,013 A | 11/1996 | Williams et al. | 424/423 |
| 5,579,773 A | 12/1996 | Vo-Dinh et al. | 128/665 |
| 5,591,422 A | 1/1997 | Hemmi et al. | 424/362 |

(Continued)

FOREIGN PATENT DOCUMENTS

| | | |
|---|---|---|
| DE | 4403789 | 8/1995 |
| WO | WO98/01131 | 1/1998 |
| WO | WO 98/48845 | * 11/1998 |
| WO | WO 99/30620 | 6/1999 |
| WO | WO 00/25665 | 5/2000 |
| WO | WO 00/25819 | 5/2000 |
| WO | WO 00/25829 | 5/2000 |
| WO | WO 02/060524 A2 | 8/2002 |

OTHER PUBLICATIONS

Fisher, A. et al, "Clinical and Preclinical Photodynamic Therapy," Lasers in Surgery and Medicine, vol. 17, pp. 2–31 (1995).

(Continued)

*Primary Examiner*—Ruth S. Smith
(74) *Attorney, Agent, or Firm*—Cook, Alex, McFarron, Manzo, Cummings & Mehler, Ltd.

(57) ABSTRACT

New contrast agents for ultrasound imaging and methods for use of such agents for imaging of human or animal tissue are described, wherein a primary active component of such medicaments is a halogenated xanthene or halogenated xanthene derivative. Preferably, the halogenated xanthene is Rose Bengal or a functional derivative of Rose Bengal.

3 Claims, 4 Drawing Sheets

U.S. PATENT DOCUMENTS

| | | | |
|---|---|---|---|
| 5,622,946 A | 4/1997 | Sessler et al. | 514/185 |
| 5,632,970 A | 5/1997 | Sessler et al. | 424/9.61 |
| 5,645,816 A | 7/1997 | Unger | 424/9.34 |
| 5,654,423 A | 8/1997 | Kahl et al. | 540/145 |
| 5,702,683 A | 12/1997 | Smith et al. | 424/9.361 |
| 5,706,810 A | 1/1998 | Rubinsky et al. | 128/653.1 |
| 5,827,186 A | 10/1998 | Chen et al. | 600/407 |
| 5,829,448 A | 11/1998 | Fisher et al. | 128/898 |
| 5,832,931 A | 11/1998 | Wachter et al. | 128/898 |
| 5,876,697 A * | 3/1999 | Soetanto | 424/9.52 |
| 5,998,597 A | 12/1999 | Fisher et al. | 536/23.1 |
| 6,036,941 A | 3/2000 | Bottiroli et al. | 424/9.6 |
| 6,042,603 A | 3/2000 | Fisher et al. | 607/89 |
| 6,063,400 A * | 5/2000 | Geho et al. | 424/9.51 |
| 6,331,286 B1 | 12/2001 | Dees et al. | 424/1.85 |
| 6,493,570 B1 | 12/2002 | Dees et al. | 600/411 |
| 2001/0041163 A1 | 11/2001 | Sugita et al. | |

OTHER PUBLICATIONS

Delprat, G.D. et al, "A New Liver Function Test, The Elimination of Rose Bengal when Injected into the Circulation of Human Subjects," Arch Intern Med, vol. 34, pp. 533–541 (1924).

Wilson, F.M., et al, "Rose Bengal Staining of Epibulbar Squamous Neoplasms," Ophthalmic Surgery, vol. 7, No. 2, pp. 21–23 (1976).

*Merck Index*, 12$^{th}$ Ed., entry 5055, 5068, 5069, 5071 (1996).

RTEC entry No. WN2817000 (N–Iodosuccinimide) and PB7000000 (Iodoform).

Young, S. et al, "Gadolinium (III) Texaphyrin: A Tumor Selective Radiation Sensitizer that is Detectable by MRI," Proc. Natl. Acad. Sci., vol. 93, pp. 6610–6615 (1996).

Bernhard, E.J. et al, "Re–Evaluating Gadolinium (III) Texaphyrin as a Radiosensitizing Agent," Cancer Research, vol. 60, pp. 86–91, (2000).

Huang, A.J.W. et al, "Photothrombosis of Corneal Neovascularization by Intravenous Rose Bengal and Argon Laser Irradiation," Arch Ophthalmol vol. 106, pp. 680–685, (1988).

Neckers, D.C., "Rose Bengal," Journal of Photochemistry and Photobiology, A: Chemistry, vol. 47, pp. 1–29 (1989).

Lindman, B. et al, *Chlorine, Bromine and Iodine NMR, Physico–Chemical and Biological Applications*, Springer–Verlag, Berlin, Germany (1976).

Engelstad, B.L. et al, "Contrast Agents," *Magnetic Resonance Imaging*, Chapter 9, pp. 161–181, C.V. Mosby Company, St. Louis, MO (1988).

Lauffer, R.B. et al, Chapter 5: "MRI Contrast Agents: Basic Principles," and Chapter 6: "Organ and Tissue Directed MRI Contrast Agents," *MRI Clinical Magnetic Resonance Imaging*, 2$^{nd}$ edition, W.B. Sanders Company, Philadelphia, PA, pp. 177–213 (1996).

Streitwieser, Jr. et al, Chapter 22: "Benzene and the Aromatic Ring," *Introduction to Organic Chemistry*, 2$^{nd}$ edition, Macmillan Publishing Company, NY, pp. 652–656 (1981).

Bezman, S.A. et al, "Photodynamic Inactivation of *E. Coli* by Rose Bengal Immobilized on Polystyrene Beads," Photochemistry and Photobiology, vol. 28, pp. 325–329 (1978).

Fluhler, E.N. et al, "Laser Intensity and Wavelength Dependence of Rose–Bengal–Photosensitized Inhibition of Red Blood Cell Acetylcholinesterase," Biochimica et Biophysica Acta, vol. 990, pp. 269–275 (1989).

Kremkau, F.W., Chapter 2: "Ultrasound," *Diagnostic Ultrasound, Principles, Instrumentation and Exercises*, 2$^{nd}$ edition, Grune & Stratton, Inc., Orlando, Florida, pp. 5–35 (1984).

PCT International Search Report dated May 7, 2004 with regard corresponding PCT application PCT/US 03/39044.

* cited by examiner

ULTRASOUND CONTRAST USING HALOGENATED XANTHENES

This is a continuation-in-part of U.S. patent application Ser. No. 09/184,388, filed on Nov. 2, 1998, now U.S. Pat. No. 6,493,570 entitled "Method for Improved Imaging and Photodynamic Therapy".

BACKGROUND OF THE INVENTION

The present invention is directed to new contrast agents for ultrasound imaging. Ultrasound imaging (and diagnostic ultrasound, hereinafter referred to collectively as ultrasound imaging) is commonly used to obtain non-invasive information about internal body structures and the function and motion of such structures. When acoustic energy is coupled into an object to be imaged (such as part of a human body), it propagates through the body with a small portion being reflected, scattered, absorbed or otherwise redirected. The properties of this propagation are affected by various acoustic variables, including pressure, density, temperature and particle motion.

A key variable affecting acoustic propagation is impedance, which comprises the product of material density and the propagation speed of acoustic energy in the material. An acoustic reflection occurs when there exists a boundary between materials of differing impedance. Thus, ultrasound imaging allows detection of impedance boundaries, such as those that occur due to the differences in density between bone and muscle or blood and vascular walls.

Considerable effort has been invested in development of ultrasound contrast agents in an effort to improve contrast between various anatomical features, such as between the vascular lumen and surrounding vessel walls. This is particularly important in assessing many myocardial, renal, respiratory, and oncologic diseases, where the ability to visualize small blood vessels enables physicians to accurately identify and assess disease severity. Moreover, when certain agents are injected directly into tissues, such as ablative agents used for destruction of diseased tissue, or instilled into internal body cavities, such as the bladder, it is desirable to be able to observe such agents using ultrasound imaging. Thus, new agents capable of exhibiting ultrasound contrast are needed for these and other medical applications of ultrasound imaging.

Therefore, it is an object of the present invention to meet these characteristics and to overcome the drawbacks in prior methods and agents.

SUMMARY OF THE INVENTION

The present invention is directed to certain ultrasound contrast agents and methods for using agents exhibiting ultrasound contrast.

In a preferred embodiment, a primary component of such ultrasound contrast agent is a halogenated xanthene or a functional derivative of a halogenated xanthene. In a further preferred embodiment, the halogenated xanthene is Rose Bengal or a functional derivative of Rose Bengal.

DETAILED DESCRIPTION OF THE PRESENTLY PREFERRED EMBODIMENT

The present invention is directed to certain ultrasound contrast agents and methods for using agents exhibiting ultrasound contrast. In a preferred embodiment, a primary component of such ultrasound contrast agent is a halogenated xanthene or a functional derivative of a halogenated xanthene. In a further preferred embodiment, the halogenated xanthene is Rose Bengal or a functional derivative of Rose Bengal (i.e., 4,5,6,7-tetrachloro-2',4',5',7'-tetraiodofluorescein).

Figure 1A:
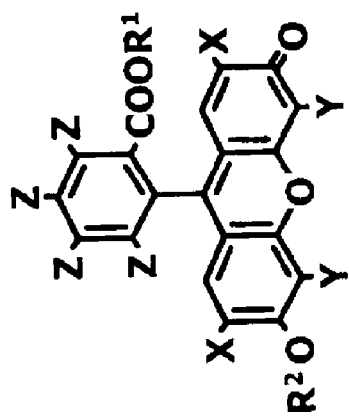
FIG. 1a is an illustration of the chemical structure of a halogenated xanthene.
Figure 1B:
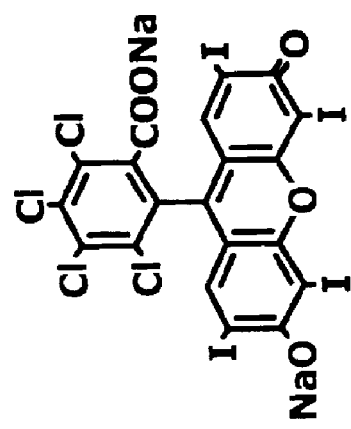
FIG. 1b is an illustration of the chemical structure of Rose Bengal.

The halogenated xanthenes constitute a family of extremely useful agents that can be selectively delivered at high concentrations to certain tissues. Certain properties of the halogenated xanthenes are described in U.S. Ser. No. 09/635,276, filed on Aug. 9,2000, and in U.S. Ser. No. 09/900,355, filed on Jul. 6, 2001, which are herein incorporated by reference in their entirety. The generalized chemical structure of the halogenated xanthenes is illustrated in FIG. 1a, where the symbols X, Y, and Z represent various elements present at the designated positions, and the symbols $R^1$ and $R^2$ represent various functionalities present at the designated positions. The chemical structure of a specific example of a halogenated xanthene, Rose Bengal, is illustrated in FIG. 1b. Physical properties of representative halogenated xanthenes are summarized in attached Table 1.

When used as a chemoablative agent, selective retention of a halogenated xanthene at a high concentration in a treated tissue can result in decreased viability or death of such tissue (and hence provides a chemotherapeutic use for medicaments containing such halogenated xanthene). When used as a photodynamic agent, selective retention of a halogenated xanthene in a treated tissue, followed by illumination of such tissue with light between 500 and 600 nm, can result in a photodynamic effect in such tissue (and hence provides a photodynamic use for medicaments containing such halogenated xanthene). When instilled into internal body cavities, such as the bladder, the distribution of the agent and the shape of the cavity may be observed. In these and various other medical applications, it may be desirable to image or otherwise monitor distribution of such medicaments during or subsequent to administration, for example to assure uniform delivery of agent to a tissue to be treated by photodynamic therapy.

The applicants have discovered that the halogenated xanthenes are capable of interacting with ultrasound to produce strong ultrasound signatures that allow detection and observation of their presence and distribution within tissue using conventional ultrasound imaging. Such properties facilitate imaging or otherwise monitoring distribution of medicaments containing such halogenated xanthenes.

The applicants speculate that this ultrasound signature arises from differences in acoustic impedance between regions of unaltered tissue (i.e., tissue not containing significant quantities of a halogenated xanthene) and regions containing halogenated xanthenes, and that such differences arise due to anomalous density of regions containing halogenated xanthenes. For example, the data in Table 2 show that a solution of 10% Rose Bengal is at least 6% more dense than saline (i.e., saline is representative of the primary interstitial fluid in tissue); in contrast, deionized water and saline have less than 1% difference in density. Since acoustic impedance, z, is directly related to density, $\bar{n}$, according to the equation $z=\bar{n}c$, where c is the propagation speed of acoustic energy in a particular medium, it is likely that the applicants' model is accurate to a first approximation.

Figure 2:
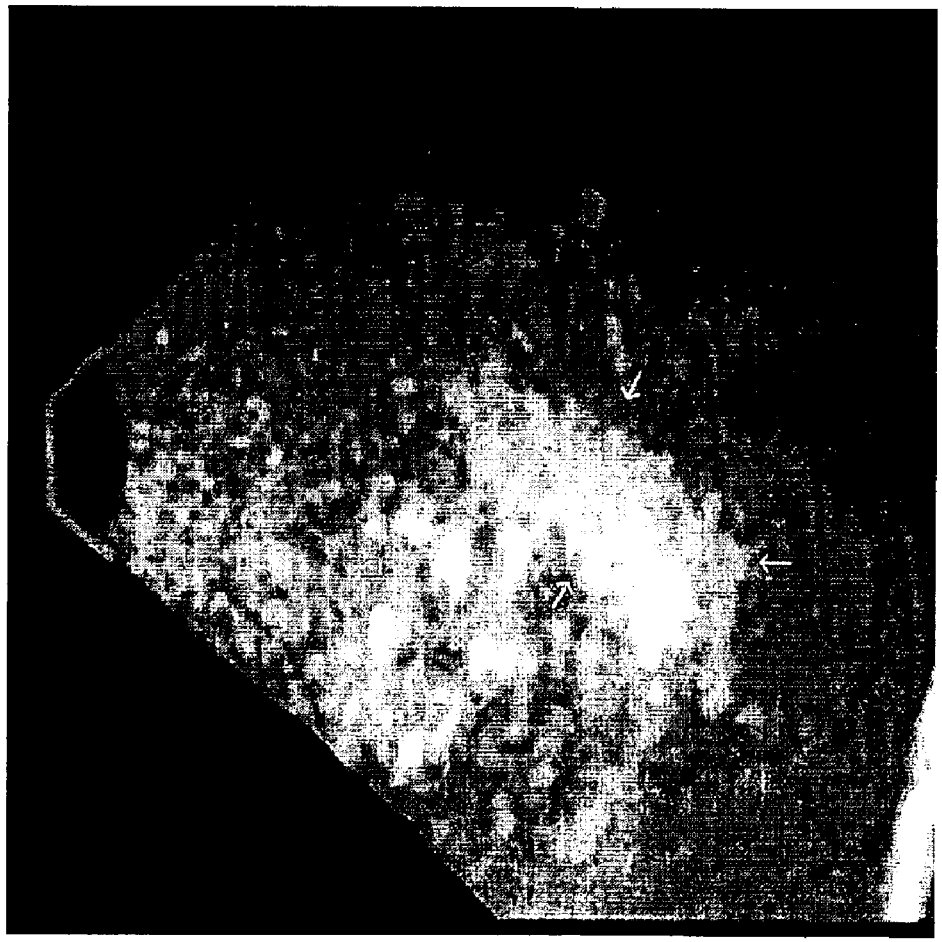
FIG. 2 illustrates an ultrasound image of a region of animal tissue following injection of a small volume of saline.
Figure 3:
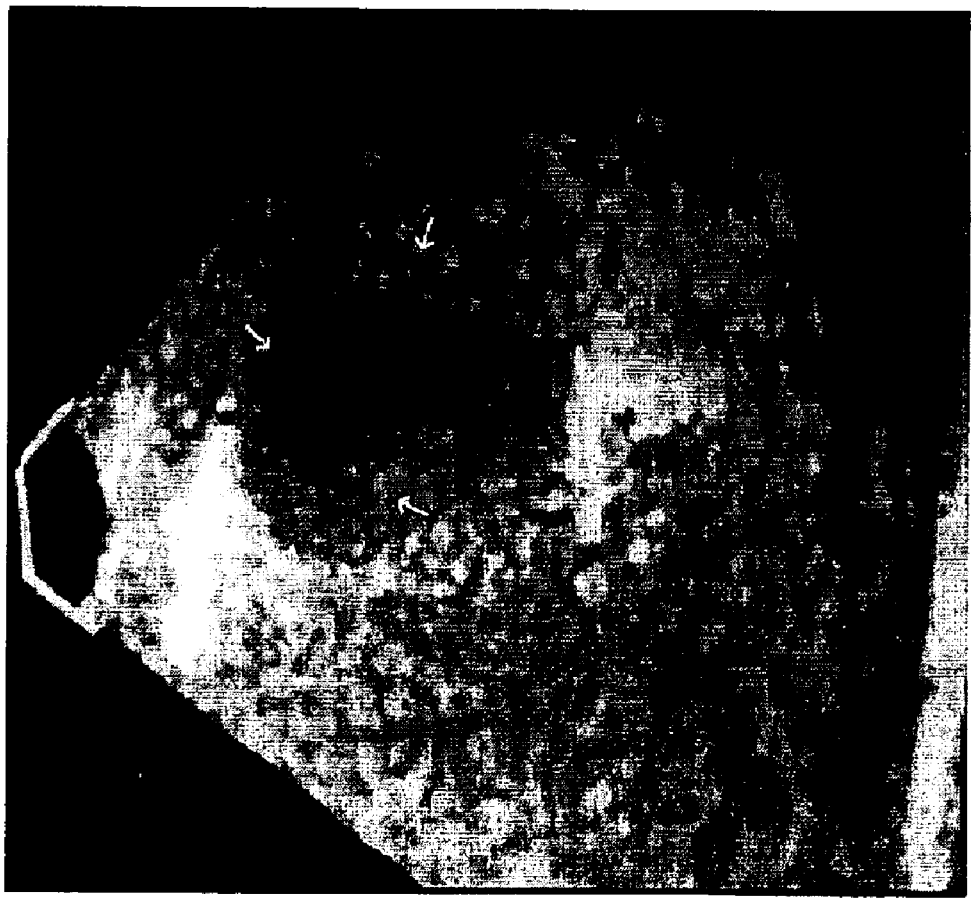
FIG. 3 illustrates an ultrasound image of a region of animal tissue following injection of a small volume of 10% Rose Bengal in saline.
Figure 4:
FIG. 4 illustrates an ultrasound image of a region of animal tissue following injection of a small volume of 20% Rose Bengal in saline.

Nonetheless, regardless of the validity of the applicants' physical model the following data vividly illustrate the applicants' observations and validate their invention. FIGS. 2, 3 and 4 illustrate ultrasound images of animal tissue following injection of a small volume of saline (i.e., FIG. 2, light region demarcated with arrows), following injection of a small volume of 10% Rose Bengal in saline (i.e., FIG. 3, dark region demarcated with arrows), and following injection of a small volume of 20% Rose Bengal in saline (i.e., FIG. 4, dark region demarcated with arrows). The tissue specimens in these examples comprise spontaneous tumor tissue in a recently deceased rat, illustrating that useful contrast can be obtained using agents containing a halogenated xanthene. Thus, a medicament containing a halogenated xanthene not only is detectable using ultrasound imaging, but is readily distinguishable from isotonic liquid (i.e., saline) and tissue. Thus, FIGS. 2–4 demonstrate that a medicament containing a halogenated xanthene may be observed and its distribution noted within tissue using conventional ultrasound imaging.

Thus, a medicament containing a halogenated xanthene can be used as an ultrasound contrast agent. Moreover, when used as a therapeutic medicament (i.e., as a chemoablative or photodynamic medicament containing a halogenated xanthene), the presence and distribution of such medicament can be monitored during, and subsequent to, administration. Such facility is useful for assuring proper delivery of such medicament.

It is thus one preferred embodiment of the present invention that an ultrasound contrast agent be produced that contains, as an active ingredient at a concentration of from greater than approximately 0.001% to less than approximately 20%, at least one halogenated xanthene.

It is further preferred that this medicament include the halogenated xanthene Rose Bengal.

Examples of other halogenated xanthenes which can be used in the medicaments of the present invention include one or more of the following: 4',5'-Dichlorofluorescein; 2',7'-Dichlorofluorescein; 4,5,6,7-Tetrachlorofluorescein; 2',4',5',7'-Tetrachlorofluorescein; Dibromofluorescein; Solvent Red 72; Diiodofluorescein; Eosin B; Eosin Y; Ethyl Eosin; Erythrosin B; Phloxine B; Rose Bengal; 4,5,6,7-Tetrabromoerythrosin; Mono-, Di-, or Tribromoerythrosin; Mono-, Di-, or Trichloroerythrosin; Mono-, Di-, or Trifluoroerythrosin; 2',7'-Dichloro-4,5,6,7-Tetrafluorofluorescein; 2',4,5,6,7,7'-Hexafluorofluorescein; 4,5,6,7-Tetrafluorofluorescein, 2',4',5,5',6,7'-Hexaiodofluorescein; 2',4',5,5',7,7'-Hexaiodofluorescein; 2',4',5',6,7,7'-Hexaiodofluorescein; 2',4',5,5',6,7,7'-Heptaiodofluorescein; 4-Chloro-2',4',5,5',6,7'-hexaiodofluorescein; 4-Chloro-2',4',5,5',7,7'-hexaiodofluorescein; 4-Chloro-2',4',5',6,7,7'-hexaiodofluorescein; 4-Chloro-2',4',5,5',6,7,7'-heptaiodofluorescein; 4,5-Dichloro-2',4',5',6,7,7'-hexaiodofluorescein; 4,6-Dichloro-2',4',5,5',7,7'-hexaiodofluorescein; and 4,7-Dichloro-2',4',5,5',6,7'-hexaiodofluoressein;

In an alternate preferred embodiment ultrasound imaging is used to image, detect or otherwise observe the presence of a medicament that contains, at a concentration of from greater than approximately 0.001% to less than approximately 20%, at least one halogenated xanthene. It is further preferred that this medicament include the halogenated xanthene Rose Bengal.

As a salient example of these preferred embodiments, certain chemoablative agents are injected into diseased tissue, such as that of liver tumors, using ultrasound imaging for guidance. A common therapeutic regimen comprises injection of a volume of concentrated ethanol into liver tumors to ablate such tumors. Unfortunately, it is difficult to visualize the delivered volume of ethanol with ultrasound imaging, making it commensurately difficult to assure that the tumor tissue has been uniformly and adequately treated. The ability to image an injected agent containing a halogenated xanthene, as illustrated in FIGS. 3 and 4 using Rose Bengal, overcomes this problem since the chemoablative agent is readily imagable using conventional ultrasound imaging.

This description has been offered for illustrative purposes only and is not intended to limit the invention of this application.

TABLE 1

Physical Properties of Some Example Halogenated Xanthenes.

| Compound | Substitution | | | | | MW (g) |
|---|---|---|---|---|---|---|
| | X | Y | Z | $R^1$ | $R^2$ | |
| 4',5'-Dichlorofluorescein | Cl | H | H | Na | Na | 445 |
| 2',7'-Dichlorofluorescein | H | Cl | H | Na | Na | 445 |
| 4,5,6,7-Tetrachlorofluorescein | H | H | Cl | H | H | 470 |
| 2',4',5',7'-Tetrachlorofluorescein | Cl | Cl | H | Na | Na | 514 |
| Dibromofluorescein | Br | H | H | Na | Na | 534 |
| Solvent Red 72 | H | Br | H | H | H | 490 |
| Diiodofluorescein | I | H | H | Na | Na | 628 |
| Eosin B | $NO_2$ | Br | H | Na | Na | 624 |
| Eosin Y | Br | Br | H | Na | Na | 692 |
| Ethyl Eosin | Br | Br | H | $C_2H_5$ | K | 714 |
| Erythrosin B | I | I | H | Na | Na | 880 |
| Phloxine B | Br | Br | Cl | Na | Na | 830 |
| Rose Bengal | I | I | Cl | Na | Na | 1018 |
| 4,5,6,7-Tetrabromoerythrosin | I | I | Br | Na | Na | 1195 |

TABLE 2

Comparison of physical properties for liquid materials

| Composition | Mass of 10 mL at 23° C. | Density Relative to Saline |
|---|---|---|
| Deionized Water | 10.002 g | −0.6% |
| Saline (0.9% Sodium Chloride) | 10.058 g | 0.0% |
| 10% Rose Bengal (w/v) in Saline (0.9% Sodium Chloride) | 10.710 g | +6.5% |

What is claimed is:

1. A method for imaging human or animal tissue comprising the steps of:

administering an ultrasound contrast agent to a patient, a portion of said ultrasound contrast agent being retained in tissue of interest; and imaging said tissue with ultrasound to identify said tissue, wherein said ultrasound contrast agent is a halogenated xanthene and said ultrasound contrast agent does not include a liposome or microbubble.

2. The method of claim 1 wherein said halogenated xanthene is present in a concentration of greater than about 0.001% to less than about 20%.

3. The method of claim 1 wherein said halogenated xanthene is Rose Bengal.

* * * * *